US009320707B2

(12) United States Patent
François et al.

(10) Patent No.: US 9,320,707 B2
(45) Date of Patent: *Apr. 26, 2016

(54) AQUEOUS SUSPENSIONS OF SUBMICRON 9-HYDROXYRISPERIDONE FATTY ACID ESTERS

(75) Inventors: Marc Karel Jozef François, Kapellen (BE); Willy Maria Albert Carlo Dries, Merksplas (BE); Esther Dina Guido Basstanie, Zandhoven (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/538,469

(22) Filed: Jun. 29, 2012

(65) Prior Publication Data

US 2012/0263795 A1  Oct. 18, 2012

Related U.S. Application Data

(63) Continuation of application No. 10/383,118, filed on Mar. 6, 2003, now abandoned, which is a continuation of application No. 09/530,687, filed as application No. PCT/EP98/07321 on Nov. 10, 1998, now Pat. No. 6,555,544.

(30) Foreign Application Priority Data

Nov. 17, 1997 (EP) ..................... 97203568

(51) Int. Cl.
| | |
|---|---|
| *A61K 31/505* | (2006.01) |
| *A01N 43/90* | (2006.01) |
| *A61K 31/519* | (2006.01) |
| *A61K 9/00* | (2006.01) |
| *A61K 9/14* | (2006.01) |

(52) U.S. Cl.
CPC .............. *A61K 9/0019* (2013.01); *A61K 9/145* (2013.01); *A61K 9/146* (2013.01); *Y10S 977/775* (2013.01); *Y10S 977/915* (2013.01); *Y10S 977/926* (2013.01)

(58) Field of Classification Search
CPC ................................... A61K 31/513
See application file for complete search history.

(56) References Cited

U.S. PATENT DOCUMENTS

| | | | |
|---|---|---|---|
| 4,485,107 A | 11/1984 | Kennis et al. |
| 4,644,000 A | 2/1987 | Gauss et al. |
| 4,665,075 A | 5/1987 | Vandenberk et al. |
| 4,804,663 A | 2/1989 | Kennis et al. |
| 5,049,322 A | 9/1991 | Devissaguet et al. |
| 5,133,908 A | 7/1992 | Stainmesse et al. |
| 5,145,684 A | 9/1992 | Liversidge et al. |
| 5,151,424 A | 9/1992 | Janssens et al. |
| 5,158,952 A | 10/1992 | Jenssen et al. |
| 5,174,930 A | 12/1992 | Stainmesse et al. |
| 5,254,556 A | 10/1993 | Janssen et al. |
| 5,260,478 A | 11/1993 | Bacon et al. |
| 5,264,610 A | 11/1993 | Bacon |
| 5,298,262 A | 3/1994 | Na et al. |
| 5,302,401 A | 4/1994 | Liversidge et al. |
| 5,318,767 A | 6/1994 | Liversidge et al. |
| 5,322,679 A | 6/1994 | Bacon et al. |
| 5,326,552 A | 7/1994 | Na et al. |
| 5,328,404 A | 7/1994 | Bacon |
| 5,330,739 A | 7/1994 | Illig |
| 5,336,507 A | 8/1994 | Na et al. |
| 5,346,702 A | 9/1994 | Na et al. |
| 5,352,459 A | 10/1994 | Hollister et al. |
| 5,384,107 A | 1/1995 | Singh et al. |
| 5,399,363 A | 3/1995 | Liversidge et al. |
| 5,401,492 A | 3/1995 | Kellar et al. |
| 5,429,824 A | 7/1995 | June |

(Continued)

FOREIGN PATENT DOCUMENTS

| | | |
|---|---|---|
| DE | 4406139 | 8/1995 |
| EP | 0196132 | 10/1986 |

(Continued)

OTHER PUBLICATIONS

Abarno AC, Comprehensive Approaches to Improving Minds and Lives, 12th Annual Meeting of the College of Psychiatric and Neurologic Pharmacists (CPNP), Jacksonville, Florida, USA, Apr. 19-22, 2009, Journal of Pharmacy Practice and Research 39 (4), p. 331-332, 2009.

Alphs L, Bossie C, Kern-Sliwa J, MA YW, Haskins JT Paliperidone Palmitate: Clinical Response in Subjects With Schizophrenia With Recent vs. Longer-Term Duration of Illness. 162nd Annual Meeting of the American Psychiatric Association (APA), San Francisco, California, USA, May 16-21, 2009. Proceedings/Abstractbook, p. 235, NO-NR6-027, 2009.

Alphs L, Bossie C, Sliwa JK, MA YW, Haskins JT Paliperidone Palmitate: Clinical Response in Subjects With Schizophrenia With Recent Diagnosis vs. Longer-Time Since Diagnosis., Poster NO-6-027 at the 162nd Meeting of the American Psychiatric Association (APA), San Francisco, California, USA, May 16-21, 2009.

Alphs L, Bossie C, Sliwa JK, MA YW, Haskins T Tolerability of Paliperidone Palmitate Initiation Doses in Subjects With Recently Diagnosed Schizophrenia. Poster NO-NR6-21 at the 163rd Annual Meeting of the American Psychiatric Association (APA), New Orleans, Louisiana, USA, May 22-26, 2010.

(Continued)

*Primary Examiner* — Alton Pryor
(74) *Attorney, Agent, or Firm* — Hal B. Woodrow

(57) ABSTRACT

The present invention is concerned with a pharmaceutical composition suitable as a depot formulation for administration via intramuscular or subcutaneous injection, comprising:
(1) as an active ingredient a therapeutically effective amount of a 9-hydroxyrisperidone fatty acid ester or a salt, or a stereoisomer or a stereoisomeric mixture thereof in submicron form and
(2) a pharmaceutically acceptable carrier; wherein the pharmaceutically acceptable carrier is water and the active ingredient is suspended therein:
and with a process of preparing such a composition.
The invention further concerns such a pharmaceutical composition for use as a medicament in the treatment of psychosis, schizophrenia, schizoaffective disorders, non-schizophrenic psychoses, behavioral disturbances associated with neurodegenerative disorders, e.g. in dementia, behavioral disturbances in mental retardation and autism, Tourette's syndrome, bipolar mania, depression, anxiety.

26 Claims, No Drawings

(56) References Cited

U.S. PATENT DOCUMENTS

| | | |
|---|---|---|
| 5,447,710 A | 9/1995 | Na et al. |
| 5,451,393 A | 9/1995 | Liversidge et al. |
| 5,453,425 A | 9/1995 | Francois et al. |
| 5,466,433 A | 11/1995 | Bacon et al. |
| 5,466,440 A | 11/1995 | Ruddy et al. |
| 5,470,583 A | 11/1995 | Na et al. |
| 5,472,683 A | 12/1995 | Illig |
| 5,488,133 A | 1/1996 | Singh et al. |
| 5,494,683 A | 2/1996 | Liversidge et al. |
| 5,500,204 A | 3/1996 | Osifo |
| 5,503,723 A | 4/1996 | Ruddy et al. |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,603,916 A | 2/1997 | Singh |
| 5,612,346 A | 3/1997 | Mesens et al. |
| 5,622,938 A | 4/1997 | Wong |
| 5,628,981 A | 5/1997 | Liversidge et al. |
| 5,643,552 A | 7/1997 | Illig |
| 5,650,173 A | 7/1997 | Ramstack et al. |
| 5,654,008 A | 8/1997 | Herbert et al. |
| 5,662,883 A | 9/1997 | Bagchi et al. |
| 5,665,330 A | 9/1997 | Wong |
| 5,665,331 A | 9/1997 | Bagchi et al. |
| 5,668,196 A | 9/1997 | Robinson et al. |
| 5,670,136 A | 9/1997 | Bacon et al. |
| 5,688,801 A | 11/1997 | Mesens et al. |
| 5,716,642 A | 2/1998 | Bagchi et al. |
| 5,718,388 A | 2/1998 | Czekai et al. |
| 5,718,919 A | 2/1998 | Ruddy et al. |
| 5,747,001 A | 5/1998 | Wiedmann et al. |
| 5,770,231 A | 6/1998 | Mesens et al. |
| 5,792,477 A | 8/1998 | Rickey et al. |
| 5,834,025 A | 11/1998 | de Garavilla et al. |
| 5,862,999 A | 1/1999 | Czekai et al. |
| 5,916,598 A | 6/1999 | Rickey et al. |
| 5,936,030 A | 8/1999 | Nicholas et al. |
| 6,045,829 A | 4/2000 | Liversidge et al. |
| 6,068,858 A | 5/2000 | Liversidge et al. |
| 6,077,843 A * | 6/2000 | François et al. ......... 514/259.41 |
| 6,165,506 A | 12/2000 | Jain et al. |
| 6,221,400 B1 | 4/2001 | Liversidge et al. |
| 6,264,922 B1 | 7/2001 | Wood et al. |
| 6,302,107 B1 | 10/2001 | Richey et al. |
| 6,323,262 B1 | 11/2001 | Achenbach et al. |
| 6,342,488 B1 | 1/2002 | Yelle |
| 6,432,381 B2 | 8/2002 | Liversidge et al. |
| 6,495,164 B1 | 12/2002 | Ramstack et al. |
| 6,500,833 B1 | 12/2002 | Yelle |
| 6,555,544 B2 * | 4/2003 | François et al. ......... 514/259.41 |
| 6,577,545 B2 | 6/2003 | Kim et al. |
| 7,521,068 B2 | 4/2009 | Bosch et al. |
| 8,293,277 B2 | 10/2012 | Swanson et al. |
| 2007/0197591 A1 | 8/2007 | Boom et al. |
| 2009/0163519 A1 | 6/2009 | Vermeulen et al. |
| 2011/0105536 A1 | 5/2011 | Lewyn-Briscoe et al. |

FOREIGN PATENT DOCUMENTS

| | | |
|---|---|---|
| EP | 368388 | * 10/1989 |
| EP | 0368388 | 5/1990 |
| GB | 2051048 | 1/1981 |
| JP | 03279324 | * 10/1991 |
| JP | 2935117 | 8/1999 |
| WO | WO 96/39397 | 12/1996 |
| WO | WO 97/44039 | 11/1997 |
| WO | WO 9844039 | * 11/1997 |
| WO | WO 2006/114384 | 11/2006 |
| WO | WO 2009/080651 | 7/2009 |

OTHER PUBLICATIONS

Alphs L, Haskins, Bossie C, Sliwa JK, Gopal S, Hough D, Davis J Long-Term Metabolic Outcomes With Paliperidone Palmitate, A Once-Monthly Long-Acting Injectable Antipsychotic Agent, in the Treatment of Subjects With Schizophrenia. Poster NO-204 at the 48th Annual Meeting of the American College of Neuropsychopharmacology (ACNP), Hollywood, Florida, USA, Dec. 6-10, 2009.

Alphs L, Samtani MN, Haskins JT, Sliwa JK, Stuyckens K, Herben V, Vermeulen A, Initiation Dosing of Deltoid Intramuscular Paliperidone Palmitate in Schizophrenia: Pharmacokinetic Rationale Based on Modeling and Simulation, 64th Annual Convention and Scientific Program of the Society of Biological Psychiatry (SOBP), Vancouver, Canada, May 14-16, 2009, Biological Psychiatry 65 (8, Suppl.), p. 213S, 2009.

Bhuvaneswar CG, Baldessarini RJ, Harsh VL, Alpert JE, Adverse Endocrine and Metabolic Effects of Psychotropic Drugs. Selective Clinical Review, CNS Drugs 23 (12), p. 1003-1021, 2009.

Bishara D, Taylor D, Upcoming Agents for the Treatment of Schizophrenia. Mechanism of Action, Efficacy and Tolerability, Drugs 68 (16), p. 2269-2292, 2008.

Bossie C, Haskins T, Sliwa JK, MA YW, Alphs L Onset of Efficacy With Paliperidone Palmitate in Patients With Acutely Exacerbated Schizophrenia. Poster NO-NR6-5 at the 163rd Annual Meeting of the American Psychiatric Association (APA), New Orleans, Louisiana, USA, May 22-26, 2010.

Chue P, Emsley R, Long-Acting Formulations of Atypical Antipsychotics. Time to Reconsider When to Introduce Depot Antipsychotics, CNS Drugs 21 (6), p. 441-448, 2007.

Citrome L, Paliperidone Palmitate—Review of the Efficacy, Safety and Cost of a New Second-Generation Depot Antipsychotic Medication, International Journal of Clinical Practice 64 (2), p. 216-239, 2010.

Citrome L, Paliperidone: Quo Vadis?, International Journal of Clinical Practice 61 (4), p. 653-662, 2007.

Cleton A, Rossenu S, Crauwels H, Berwaerts J, Hough D, Gopal S, Eerdekens M, Vandebosch A, Rosso Fernandez C Assessment of the Dose Proportionality of Paliperidone Palmitate 25, 50, 100 and 150 MG EQ., A New Long-Acting Injectable Antipsychotic, Following Administration in the Deltoid or Gluteal Muscles. Poster at the 2008 Annual Meeting of the American Society for Clinical Pharmacology and Therapeutics (ASCPT), Orlando, Florida, USA, Apr. 2-5, 2008.

Cleton A, Rossenu S, Hough D, Crauwels H, Berwaerts J, Gopal S, Vandebosch A, Rosso Fernandez C, Assessment of the Dose Proportionality of Paliperidone Palmitate 25, 50, 100 and 150 MG EQ., A New Long-Acting Injectable Antipsychotic Following Administration in the Deltoid or Gluteal Muscles, 2008 Annual Meeting of the American Society for Clinical Pharmacology and Therapeutics (ASCPT), Orlando, Florida, USA, Apr. 2-5, 2008, Clinical Pharmacology and Therapeutics 83 (Suppl.1), p. S31, 2008.

Cleton A, Rossenu S, Hough D, Crauwels H, Vandebosch A, Berwaerts J, Eerdekens M, Francetic I Evaluation of the Pharmacokinetic Profile of Deltoid Versus Gluteal Intramuscular Injections of Paliperidone Palmitate in Patients with Schizophrenia. Poster at the 2008 Annual Meeting of the American Society for Clinical Pharmacology and Therapeutics (ASCPT), Orlando, Florida, USA, Apr. 2-5, 2008.

Cleton A, Rossenu S, Hough D, Crauwels H, Vandebosch A, Berwaerts J, Eerdekens M, Francetic I, Evaluation of the Pharmacokinetic Profile of Gluteal Versus Deltoid Intramuscular Injections of Paliperidone Palmitate 100 MG Equivalent in Patients

(56) References Cited

OTHER PUBLICATIONS with Schizophrenia, 2008 Annual Meeting of The American Society for Clinical Pharmacology and Therapeutics (ASCPT), Orlando, Florida, USA, Apr. 2-5, 2008, Clinical Pharmacology and Therapeutics 83 (Suppl.1), p. S31, 2008.
Coppola D, Liu Y, Gopal S, Remmerie B, Samtani M, Pandina G, Hough D, Nuamah I, Sulaiman A Long-Term Safety, Tolerability and Pharmacokinetics of Paliperidone Palmitate. A One-Year Open-Lable Study in Patients with Schizophrenia. Poster NO-NR6-7 at the 163rd Annual Meeting of the American Psychiatric Association (APA), New Orleans, Louisiana, USA, May 22-26, 2010.
Coppola D, Liu Y, Gopal S, Remmerie B, Samtani M, Pandina G, Hough D, Nuamah I, Sulaiman A Long-Term Safety, Tolerability and Pharmacokinetics of Paliperidone Palmitate 234 MG (150 MG EQ.), The Highest Marketed Dose: A One-Year Open-Label Study in Patients with Schizophrenia. Poster NO-PI-49 at the 2010 Annual Meeting of the American Society for Clinical Pharmacology and Therapeutics (ASCPT), Atlanta, Georgia, USA, Mar. 17-20, 2010.
Coppola D, Liu Y, Gopal S, Remmerie B, Samtani M, Pandina G, Hough D, Nuamah I, Sulaiman A, Long-Term Safety, Tolerability and Pharmacokinetics of Paliperidone Palmitate: A One-Year Open-Lable Study in Patients with Schizophrenia, 2010 Annual Meeting of the American Society for Clinical Pharmacology and Therapeutics (ASCPT), Atlanta, Georgia, USA, Mar. 17-20, 2010, Clinical Pharmacology and Therapeutics 87 (Suppl.1), p. S25, 2010.
Davidson M, Emsley R, Kramer M, Ford L, Pan G, Lim P, Eerdekens M, Efficacy, Safety and Early Response of Paliperidone Extended-Release Tablets (Paliperidone ER): Results of a 6-Week, Randomized, Placebo-Controlled Study, Schizophrenia Research 93 (1-3), p. 117-130 [Erratum: 96 (1-3), P. 272-274], 2007.
Dlugosz H, Nasrallah HA, Paliperidone: A New Extended-Release Oral Atypical Antipsychotic, Expert Opinion on Pharmacotherapy 8 (14), p. 2307-2313, 2007.
Dopheide JA, Paliperidone: An Improvement Over Risperidone?, American Journal of Health-System Pharmacy 65 (5), p. 401, 2008.
Emsley R, Drugs in Development for the Treatment of Schizophrenia, Expert Opnion on Investigational Drugs 18 (8), p. 1103-1118, 2009.
Fleischhacker W, Gopal S, Samtani MN, Quiroz JA, Pandina G, Vermeulen A, Herben V, Gassmann-Mayer C, Lim P, Kusumakar V, Palumbo J., Optimization of the Dosing Strategy for the Long-Acting Injectable Antipsychotic Paliperidone Palmitate: Results of two Randomized Double-Blind Studies and Population Pharmacokinetic Simulations, 47th Annual Meeting of the American College of Neuropsychopharmacology (ACNP), Scottsdale, Arizona, USA, Dec. 7-11, 2008, Proceedings/Abstractbook, 2008.
Fleischhacker WW, Gopal S, Samtani MN, Quiroz JA, Pandina G, Vermeulen A, Herben V, Gassmann-Mayer C, Lim P, Kusumakar V, Palumbo J Optimization of the Dosing Strategy for the Long-Acting Injectable Antipsychotic Paliperidone Palmitate: Results of two Randomized Double-Blind Studies and Population Pharamacokinetic Simulations. Poster NO-21 at the 47th Annual Meeting of the American College of Neuropsychopharmacology (ACNP), Scottsdale, Arizona, USA, Dec. 7-11, 2008.
Fleischhacker WW, Gopal S, Samtani MN, Quiroz JA, Pandina G, Vermeulen A, Herben V, Gassmann-Mayer C, Lim P, Kusumakar V, Palumbo J Optimization of the Dosing Strategy for the Long-Acting Injectable Antipsychotic Paliperidone Palmitate: Results of two Randomized Double-Blind Studies and Population Pharmacokinetic Simulations. Poster NO-1-027 at the 162nd Annual Meeting of the American Psychiatric Association (APA), San Francisco, California, USA, May 16-21, 2009.
Fleischhacker WW, Gopal S, Samtani MN, Quiroz JA, Pandina G, Vermeulen A, Herben V, Gassmann-Mayer C, Lim P, Kusumakar V, Palumbo J, Optimization of Dosing Strategy for Paliperidone Palmitate in Schizophrenia: Results of Double-Blind Studies and Population Pharmacokinetic Simulations, 162nd Annual Meeting of the American Psychiatric Association (APA), San Francisco, California, USA, May 16-21, 2009, Proceedings/Abstractbook, p. 11-12, NO-NR1-027, 2009.

Fleischhacker WW, Second-Generation Antipsychotic Long-Acting Injections: Systematic Review, British Journal of Psychiatry 195 (Suppl.52), p. S29-S36, 2009.
Fu D, Wang D, Li Q, Berwaerts J, Wu X, Favis R, Haas M, Turner N, Chung H, Alphs L, Manji H, Twyman R, Cohen N, Genetic Variation in ERBB4 Gene Associated with Response to Paliperidone Treatment in Patients with Schizophrenia, 17th World Congress on Psychiatric Genetics (WCPG), San Diego, California, USA, Nov. 4-8, 2009, Proceedings/Abstractbook, NO-199, 2009.
Fu DJ, Wang D, Li Q, Berwaerts J, Wu X, Favis R, Haas M, Turner N, Chung H, Alphs L, Manji H, Twyman R Cohen N Genetic Variation in ERBB4 Gene Associated with Response to Paliperidone Treatment in Patients with Schizophrenia. Poster NO-199 on the 17th World Congress on Psychiatric Genetics (WCPG), San Diego, California, USA, Nov. 4-8, 2009.
Gopal S, Berwaerts J, Nuamah I, Akhras K, Coppola D, Daly E, Hough DW, Palumbo JM Efficacy and Safety of Long-Acting Injectable Paliperidone Palmitate Relative to Long-Acting Injectable Haloperidol, Bromperidol and Fluphenazine Decanoate for Long-Term Treatment in Patients with Schizophrenia Using Number Needed to Treat and Number Needed to Harm. Poster at the 12th Annual Meeting of the American Society for Experimental Neurotherapeutics (Asent), Bethesda, Maryland, USA, Mar. 4-6, 2010.
Gopal S, Berwaerts J, Nuamah I, Akhras K, Coppola D, Daly E, Hough DW, Palumbo JM Efficacy and Safety of Long-Acting Injectable Paliperidone Palmitate Relative to Long-Acting Haloperidol, Bromperidol and Fluphenazine Decanoate for Long-Term Treatment in Patients with Schizophrenia using Number Needed to Treat and Number Needed to Harm. Poster at the 65th Annual Convention and Scientific Program of the Society of Biological Psychiatry (SOBP), New Orleans, Louisiana, USA, May 20-22, 2010.
Gopal S, Gassmann-Mayer C, Palumbo J, Samtani MN, Shiwach R, Alphs L, Practical Guidance for Dosing and Switching Paliperidone Palmitate Treatment in Patients with Schizophrenia, Current Medical Research and Opinion 26 (2), p. 377-387, 2010.
Gopal S, Lindenmayer JP, Hough D, Melkote R, Lim P, Eerdekens M, Safety and Tolerability of Paliperidone Palmitate Injected in the Deltoid or Gluteus Muscle in Patients with Schizophrenia, 161st Meeting of the American Psychiatric Association (APA), Washington, DC, USA, May 3-8, 2008, Proceedings/Abstractbook, p. 205-206, NO-NR4-100, 2008.
Gopal S, Lindenmayer JP, Hough D, Melkote R, Lim P, Eerdekens M, Safety and Tolerability of the Investigational Antipsychotic Paliperidone Palmitate Injected in the Deltoid or Gluteus Muscle in Patients with Schizopherenia, 63rd Annual Convention and Scientific Program of the Society of Biological Psychiatry (SOBP), Washington, DC, USA, May 1-3, 2008, Biological Psychiatry 63 (7, Suppl.7), p. 285S, 2008.
Gopal S, Lindenmayer JP, Hough D, Melkote R, Lim P, Yuen E, Palumbo J, Eerdekens M Safety and Tolerability Profiles of Paliperidone Palmitate Injected into Either the Deltoid or Gluteus Muscle in Patients with Schizophrenia. Poster NO-161 at the 60th Annual Meeting of the American Psychiatric Association (APA), Institute on Psychiatric Services (IPS), Oct. 2-5, 2008.
Gopal S, Lindenmayer JP, Hough D, Melkote R, Lim P, Yuen E, Palumbo J, Eerdekens M Safety and Tolerability Profiles of Paliperidone Palmitate Injected into Either the Deltoid or Gluteus Muscle in Patients with Schizophrenia. Poster NO-4-100 at the 161st Meeting of the American Psychiatric Association (APA), Washington, DC, USA, May 3-8, 2008.
Gopal S, Lindenmayer JP, Hough D, Melkote R, Lim P, Yuen E, Palumbo J, Eerdekens M Safety and Tolerability Profiles of Paliperidone Palmitate Injected into Either the Deltoid or Gluteus Muscle in Patients with Schizophrenia. Poster at the 63rd Annual Convention and Scientific Program of the Society of Biological Psychiatry (SOBP), Washington, DC, USA, May 1-3, 2008.
Gopal S, Vijapurkar U, Lim P, Morozova M, Eerdekens M Long-Term Efficacy, Safety and Tolerability of Paliperidone Palmitate in Patients with Schizophrenia. Poster NO-1-031 at the 162nd Annual Meeting of the American Psychiatric Association (APA), San Francisco, California, USA, May 16-21, 2009.

(56) References Cited

OTHER PUBLICATIONS

Gopal S, Vijapurkar U, Lim P, Morozova M, Eerdekens M Long-Term Efficacy, Safety and Tolerability of Paliperidone Palmitate in Patients with Schizophrenia. Poster NO-20 at the 12th Annual Meeting of the College of Psychiatric and Neurologic Pharmacists (CPNP), Jacksonville, Florida, Apr. 19-22, 2009.

Gopal S, Vijapurkar U, Lim P, Morozova M, Eerdekens M, Long-Term Efficacy, Safety, and Tolerability of Paliperidone Palmitate in Patients With Schizophrenia, 12th Annual Meeting of the College of Psychiatric and Neurologic Pharmacists (CPNP), Jacksonville, Florida, Apr. 19-22, 2009, Journal of Pharmacy Practice 22 (2), p. 217 [Errratum: 22 (4), p. 432], 2009.

Gopal S, Vijapurkar U, Lim P, Morozova M, Eerdekens M, Long-Term Efficacy, Safety, and Tolerability of Paliperidone Palmitate in Patients with Schizophrenia, 162nd Annual Meeting of the American Psychiatric Association (APA), San Francisco, California, USA, May 16-21, 2009, Proceedings/Abstractbook, p. 13, NO-1-031, 2009.

Green B, Paliperidone: A Clinical Review, Current Drug Therapy 4, p. 7-11, 2009.

Haskins JT, Samtani MN, Alphs L, Sliwa JK, Stuyckens K, Herben V, Vermeulen A, Maintenance Dosing of Once-Monthly (4-Weekly) Paliperidone Palmitate in Schizophrenia: Pharmacokinetic Rationale Based on Population Based Simulations, 162nd Annual Meeting of the American Psychiatric Association (APA), San Francisco, California, USA, May 16-21, 2009, Proceedings/Abstractbook, p. 15, NO-1-036, 2009.

Haskins JT, Sliwa JK, MA YW, Pandina GJ, Palumbo J Efficacy and Safety of 234 MG Initiation Dose and 3-Fixed Maintenance Doses of Paliperidone Palmitate—A Once-Monthly Injectable Atypical Antipsychotic. Poster NO-123 at the 22nd US Psychiatric and Mental Health Congress (USPMHC), Las Vegas, Nevada, USA, Nov. 2-5, 2009.

Haskins JT, Sliwa JK, MA YW, Pandina GJ, Palumbo J Efficacy and Safety of 234 MG Initiation Dose and 3-Fixed Maintenance Doses of Paliperidone Palmitate—A New Once-Monthly Injectable Atypical Antipsychotic. 22nd US Psychiatric and Mental Health Congress (USPMHC), Las Vegas, Nevada, USA, Nov. 2-5, 2009.

Hough D, Gopal S, Vijapurkar U, Lim P, Morozova M, Eerdekens M, Eeerdekens M Paliperidone Palmitate, An Atypical Infectable Antipsychotic, In Prevention of Symptom Recurrence in Patients with Schizophrenia: A Randomized, Double-Blind, Placebo Controlled Study. Poster at the 60th Annual Meeting of the American Psychiatric Association (APA), Institute on Psychiatric Services (IPS), Chicago, Illinois, USA, Oct. 2-5, 2008.

Hough D, Gopal S, Vijapurkar U, Lim P, Morozova M, Eerdekens M, Eerdekens M Paliperidone Palmitate, An Atypical Injectable Antipsychotic, In Prevention of Symptom Recurrence in Patients with Schizophrenia: A Randomized, Double-Blind, Placebo Controlled Study. Poster NO-4-029 at the 161st Meeting of the American Psychiatric Association (APA), Washington, DC, USA, May 3-8, 2008.

Hough D, Gopal S, Vijapurkar U, Lim P, Morozova M, Eerdekens M Paliperidone Palmitate, An Atypical Injectable Antipsychotic, In Prevention of Symptom Recurrence in Patients with Schizophrenia: A Randomized, Double-Blind, Placebo Controlled Study. Poster at the 63rd Annual Convention and Scientific Program of the Society of Biological Psychiatry (SOBP), Washington, DC, USA, May 1-3, 2008.

Hough D, Gopal S, Vijapurkar U, Lim P, Morozova M, Eerdekens M, Paliperidone Palmitate in Prevention of Symptom Recurrence in Patients with Schizophrenia: A Randomized, Double-Blind, Placebo-Controlled Study, 161st Meeting of the American Psychiatric Association (APA), Washington, DC, USA, May 3-8, 2008, Proceedings/Abstractbook, p. 173, NO-NR4-029, 2008.

Hough D, Gopal S, Vijapurkar U, Lim P, Morozova M, Eerdekens M, Paliperidone Palmitate Maintenznce Treatment in Delaying the Time-to-Relapse in Patients with Schizophrenia: A Randomized, Double-Blind, Placebo-Controlled Study, Schizophrenia Research 116 (2-3), p. 107-117, 2010.

Hough D, Gopal S, Vijapurkar U, Lim P, Morozova M, Eerdekens M, Paliperidone Palmitate, an Injectable antipsychotic, in Prevention of Symptom Recurrence in Patients with Schizophrenia: A Randomized, Double-Blind, Placebo-Controlled Study, 63rd Annual Convention and Scientific Program of the Society of Biological Psychiatry (SOBP), Washington, DC, USA, May 1-3, 2008, Biological Psychiatry 63 (7, SUPPL.7), p. 285S-286S, 2008.

Hough D, Lindenmayer JP, Gopal S, Melkote R, Lim P, Herben V, Yuen E, Eerdekens M, Safety and Tolerability of Deltoid and Gluteal Injections of Paliperidone Palmitate in Schizophrenia, Progress in Neuro-Psychopharmacology and Biological Psychiatry 33 (6), p. 1022-1031, 2009.

Hoy SM, Scott LJ, Keating GM, Intramuscular Paliperidone Palmitate, CNS Drugs 24 (3), p. 227-244, 2010.

Janicak PG, Winans EA, Paliperidone ER: A Review of the Clinical Trial Data, Neuropsychiatric Disease and Treatment 3 (6), p. 869-883, 2007.

Jefferson JW, Innovative Delivery Technologies for Psychiatric Drugs, International Drug Therapy Newsletter 41 (12), p. 91-96, 2006.

Kane J, Canas F, Kramer M, Ford L, Gassmann-Mayer C, Lim P, Eerdekens M, Treatment of Schizophrenia with Paliperidone Extended-Release Tablets: A 6-Week Placebo-Controlled Trial, Schizophrenia Research 90 (1-3), p. 147-161, 2007.

Kane JM, Garcia-Ribera C, Clinical Guideline Recommendations for Antipsychotic Long-Acting Injections, British Journal of Psychiatry 195 (SUPPL.52), p. S63-S67, 2009.

Kane JM, Leucht S, Marder SR, Robinson DG, Siegel S, New Developments in the Treatment of Schizophrenia, Teleconference Series "New Developments in the Treatment of Schizophrenia", Sep. 2006, Journal of Clinical Psychiatry 68 (3), p. 463-478, 2007.

Kozma C, Dirani R, Nicholl D, Akhras K Evaluation of the Relationships Among Change in Function, Symptoms, and Duration of Schizophrenia. Poster NO-NR6-4 at the 163rd Annual Meeting of the American Psychiatric Association (APA), New Orleans, Louisiana, USA, May 22-26, 2010.

Kramer M, Lim P, Eerdekens M, Hough D, Litman R, Lane R, Palumbo J Efficacy/Tolerability of Paliperidone Palmitate: 9-Week, Placebo-Controlled Study in Schizophrenia Patients. Poster NO-322 at the 14th Biennial Winter Workshop on Schizophreniz and Biopolar Disorders (WWS), Montreux, Switzerland, Feb. 3-7, 2008.

Kramer M, Litman R, Hough D, Lane R, Lim P, Eerdekens M A 9-Week, Placebo-Controlled Study in Schizophrenia Patients: Efficacy and Safety of the Long-Acting Injectable Agent, Paliperidone Palmitate. Poster NO-4-072 at the 161st Meeting of the American Psychiatric Association (APA), Washington, DC, USA, May 3-8, 2008.

Kramer M, Litman R, Hough D, Lane R, Lim P, Eerdekens M, A 9-Week, Placebo-Controlled Study in Schizophrenia Patients: Efficacy and Safety of the Long-Acting Injectable Agent, Paliperidone Palmitate, 161st Meeting of the American Psychiatric Association (APA), Washington, DC, USA, May 3-8, 2008, Proceedings/Abstractbook, p. 192-193, NO-NR4-072, 2008.

Kramer M, Litman R, Hough D, Lane R, Lim P, Liu Y, Eerdekens M, Paliperidone Palmitate, A Potential Long-Acting Treatment for Patients with Schizophrenia. Results of a Randomized, Double-Blind, Placebo-Controlled Efficacy and Safety Study, The Intenational Journal of Neuropsychopharmacology 13 (5), p. 635-647, 2010.

Kramer M, Litman R, Lane R, Kujawa M, Lim P, Hough D, Eerdekens M, Efficacy/Tolerability of Paliperidone Palmitate: 9-Week, Placebo-Controlled Study in Schizophrenia Patients, 14th Biennial Winter Workshop on Schizophreniz and Bipolar Disorders (WWS), Montreaux, Switzerland, Feb. 3-7, 2008, Schizophrenia Research 98 (SUPPL.1), p. 165-166, 2008.

Kramer M, Litman R, Lane R, Lim P, Hough D, Eerdekens M Efficacy and Tolerability of Paliperidone Palmitate: 9-Week, Placebo-Controlled Study in Schizophrenia Patients. Poster at the 63rd Annual Convention and Scientific Program of the Society of Biological Psychiatry (SOBP), Washington, DC, USA, May 1-3, 2008.

Kramer M, Litman R, Lane R, Lim P, Hough D, Palumbo J, Eerdekens M Efficacy and Tolerability of Two Fixed Dosages of Paliperidone Palmitate in the Treatment of Schizophreniz: Results of

(56) References Cited

OTHER PUBLICATIONS a 9-Week Placebo-Controlled Trial. Poster at the 20th US Psychiatric and Mental Health Congress (USPMHC), Orlando, Florida, USA, Oct. 11-14, 2007.
Kramer M, Litman RE, Lane R, Lim P, Hough D, Eerdekens M, Efficacy and Tolerability of Paliperidone Palmitate: 9-Week, Placebo-Controlled Study in Schizophrenia Patients, 63rd Annual Convention and Scientific Program of the Society of Biological Psychiatry (SOBP), Washington, DC, USA, May 1-3, 2008, Biological Psychiatry 63 (7, SUPPL.7), p. 288S, 2008.
Lindenmayer JP, Long-Acting Injectable Antipsychotics: Focus on Olanzapine Pamoate, Neuropsychiatric Disease and Treatment 6, p. 261-267, 2010.
Madhusoodanan S, Zaveri D, Paliperidone use in the Elderly, Current Drug Safety 5, p. 149-152, 2010.
Nasrallah HA, Gopal S, Gassmann-Mayer C, Quiroz JA, Lim P, Eerdekens M, Yuen E, Palumbo J, Hough D Efficacy and Safety of Three Doses of Paliperidone Palmitate, an Investigational Long Acting Injectable Antipsychotic, in Schizophrenia. Poster NO-4-036 at the 161st Meeting of the American Psychiatric Association (APA), Washington, DC, USA, May 3-8, 2008.
Nasrallah HA, Gopal S, Gassmann-Mayer C, Quiroz JA, Lim P, Eerdekens M, Yuen E, Palumbo J, Hough D Efficacy and Safety of Three Doses of Paliperidone Palmitate, an Investigatinal Long Acting Injectable Antipsychotic, in Schizophrenia. Poster NO-125 at the 60th Annual Meeting of the American Psychiatric Association (APA), Institute on Psychiatric Services (IPS), Chicago, Illinois, USA, Oct. 2-5, 2008., 2008.
Nasrallah HA, Gopal S, Quiroz JA, Gassmann-Mayer C, Lim P, Eerdekens M, Hough D, Efficacy and Safety of Three Doses of Paliperidone Palmitate, an Investigational Long-Acting Injectable Antipsychotic, in Schizophrenia, 161st Meeting of the American Psychiatric Association (APA), Washington, DC, USA, May 3-8, 2008, Proceedings/Abstractbook, p. 176-177, NO-NR4-036, 2008.
Nicholl D, Nasrallah H, Nuamah I, Akhras K, Gagnon DD, Gopal S, Personal and Social Functioning in Schizophrenia: Defining a Clinically Meaningful Measure of Maintenance in Relapse Prevention, Current Medical Research and Opinion 26 (6), p. 1471-1484, 2010.
Nussbaum A, Stroup TS, Paliperidone for Schizophrenia (Review), The Cochrane Library (3), p. 1-147, 2008.
Oberpichler-Schwenk H, Paliperidone BEI Schizophrenie. (Paliperidon in Schizophrenia), Psychopharmakotherapie 13 (6), p. 265-267, 2006.
Pandina G, Lane R, Gopal S, Gassmann-Mayer C, Hough D, Remmerie B, Simpson G a Randomized, Double-Blind, Comparative Study of Flexible Doses of Paliperidone Palmitate and Risperidone Long-Acting Therapy in Patients with Schizophrenia. Poster at the 48th Annual Meeting of the American College Neuropsychopharmacology (ACNP), Hollywood, Florida, USA, Dec. 6-10, 2009.
Pandina G, Lane R, Gopal S, Gassmann-Mayer C, Hough D, Remmerie B, Simpson G A Randomized, Double-Blind, Study of Flexible Doses of Paliperidone Palmitate and Risperidone Long-Acting Therapy in Patients with Schizophrenia. Poster at the 65th Annual Convention and Scientic Program of the Society of Biological Psychiatry (SOBP), New Orleans, Louisiana, USA, May 20-22, 2010.
Pandina G, Lindenmayer J, Lull J, Lim P, Gassmann-Mayer C, Yuen E, Palumbo J, Gopal S, A Randomized, Double-Blind, Placebo-Controlled, Dose-Response Study to Assess Efficacy and Safety of Paliperidone Palmitate in Adult Subjects with Schizophrenia, 12th International Congress on Schizophrenia Research (ICOSR), San Diego, California, USA, Mar. 28-Apr. 1, 2009, Schizophrenia Bulletin 35 (SUPPL.1), p. 370, 2009.
Pandina G, Lindemayer JP, Lull J, Lim P, Gassmann-Mayer C, Gopal S, Yuen E, Palumbo J, A Randomized, Double-Blind, Placebo-Controlled, Dose-Response Efficacy/Safety Study of Paliperidone Palmitate in Adults with Schizophrenia, 162nd Annual Meeting of The American Psychiatric Association (APA), San Francisco, California, USA, May 16-21, 2009, Proceedings/Abstractbook, p. 30, NO-NR1-073, 2009.
Pandina GJ, Lindenmayer JP, Lull J, Lim P, Gopal S, Herben V, Kusumakar V, Yuen E, Palumbo J a Randomized, Double-Blind, Placebo-Controlled, Dose-Response Efficacy and Safety Study of Paliperidone Palmitate in Adults With Schizophrenia Poster NO-1-073 at the 162nd Annual Meeting of the American Psychiatric Association (APA), San Francisco, California, USA, May 16-21, 2009.
Pandina GJ, Lindenmayer JP, Lull J, Lim P, Gopal S, Herben V, Kusumakar V, Yuen E, Palumbo J, a Randomized, Placebo-Controlled Study to Assess the Efficacy and Safety of 3 Doses of Paliperidone Palmitate in Adults With Acutely Exacerbated Schizophrenia, Journal of Clinical Psychopharmacology 30 (3), p. 235-244, 2010.
Pandina GJ, Lindenmayer JP, Lull J, Lim P, Gopal S, Kusumakar V, Yuen E, Palumbo J a Randomized, Placebo-Controlled Study to Assess the Efficacy and Safety of Three Doses of Paliperidone Palmitate in Adults With an Acute Exacerbation of Schizophrenia. Poster at the 12th International Congress on Schizophrenia Research (ICOSR), San Diego, California, USA, Mar. 28-Apr. 1, 2009.
Pandina GJ, Lindenmayer JP, Lull J, Lim P, Gopal S, Kusumakar V, Yuen E, Palumbo J a Randomized, Placebo-Controlled Study to Assess the Efficacy and Safety of Three Doses of Paliperidone Palmitate in Adults With an Acute Exacerbation of Schizophrenia. Poster at the 12th Annual Meeting of the College of Psychiatric and Neurologic Pharmacists (CPNP), Jacksonville, Florida, Apr. 19-22, 2009.
Revill P, Serradell N, Bolos J, Paliperidone—Antipsychotic Agent, Treatment of Bipolar Disorder, Dual Dopamine D2/5-HT2A Receptor Antagonist, Drugs of the Future 31 (7), p. 579-584, 2006.
Samtani MN, Alphs L, Sliwa JK, Stuyckens K, Herben V, Vermeulen a Maintenance Dosing of the Once-Monthly (4-Weekly) Paliperidone Palmitate in Schizophrenia: Pharmacokinetic Rationale Based on Population Simulations. Poster NO-1-036 at the 162nd Annual Meeting of the American Psychiatric Association (APA), San Francisco, California, USA, May 16-21, 2009.
Samtani MN, Gopal S, Kern Sliwa J, Haskins JT, Alphs L, Stuyckens K, Vermeulen a Management of Missed Paliperidone Palmitate Doses Based on Pharmacokinetic Modeling and Simulation. Poster at the 49th Annual Meeting of the New Clinical Drug Evaluation Unit (NCDEU) of the National Institute of Mental Health (NIMH), Hollywood, Florida, USA, Jun. 29-Jul. 2, 2009.
Samtani MN, Gopal S, Kern Sliwa J, Haskins JT, Alphs L, Stuyckens K, Vermeulen a Switching to Paliperidone Palmitate From Other Antipsychotics: Guidance Based on Pharmacokinetic Modeling and Simulation. Poster No. I-68 at the 49th Annual Meeting of the New Clinical Drug Evaluation Unit (NCDEU) of the National Institute of Mental Health (NIMH), Hollywood, Florida, USA, Jun. 29-Jul. 2, 2009.
Samtani MN, Gopal S, Kern Sliwa J, Haskins JT, Alphs L, Stuyckens K, Vermeulen A, Management of Missed Paliperidone Palmitate Doses Based on Pharmacokinetic Modeling and Simulation, 49th Annual Meeting of the New Clinical Drug Evaluation Unit (NCDEU) of the National Institute of Mental Health (NIMH), Hollywood, Florida, USA, Jun. 29-Jul. 2, 2009, Proceedings/Abstractbook, p. 140, 2009.
Samtani MN, Gopal S, Kern Sliwa J, Haskins JT, Alphs L, Stuyckens K, Vermeulen A, Switching to Paliperidone Palmitate From Other Antipsychotics: Guidance Based on Pharmacokinetic Modeling and Simulation, 49th Annual Meeting of the New Clinical Drug Evaluation Unit (NCDEU) of the National Institute of Mental Health (NIMH), Hollywood, Florida, USA, Jun. 29-Jul. 2, 2009, Proceedings/Abstractbook, p. 68, 2009.
Asmtani MN, Gopal S, Kern Sliwa J, Haskins T, Alphs L, Stuyckens K, Vermeulen a Paliperidone Palmitate Dosing in Special Patient Populations Including the Elderly and Those with Renal Impairment or Differing Body Mass Index: Guidance Based on Pharmacokinetic Modeling and Simulation. Poster at the American Conference on Pharmacometrics, Mashantucket, Connecticut, USA, Oct. 4-7, 2009.
Samtani MN, Haskins JT, Alphs L, Sliwa JK, Stuyckens K, Herben V, Vermeulen a Maintenance Dosing of Once-Monthly (4-Weekly) Paliperidone Palmitate in Schizophrenia: Pharmacokinetic Rationale Based on Population Simulations. Poster NO-21 at the 12th Annual Meeting of the College of Psychiatric and Neurologic Pharmacists (CPNP), Jacksonville, Florida, Apr. 19-22, 2009.

(56) References Cited

OTHER PUBLICATIONS

Samtani MN, Haskins JT, Alphs L, Sliwa JK, Stuyckens K, Herben V, Vermeulen A, Maintenance Dosing of Once-Monthly (4-Weekly) Paliperidone Palmitate in Schizophrenia: Pharmacokinetic Rationale Based on Population-Based Simulations, 12th Annual Meeting of the College of Psychiatric and Neurologic Pharmacists (CPNP), Jacksonville, Florida, Apr. 19-22, 2009, Journal of Pharmacy Practice 22 (2), p. 218 [ERRATUM: 22 (4), p. 432], 2009.
Samtani MN, Haskins JT, Alphs L, Stuyckens K, Herben V, Vermeulen a Initiatin Dosing of Deltoid Intramuscular Paliperidone Palmitate in Schizophrenia: Pharmacokinetic Rationale Based on Modeling and Simulation. Poster NO-1-046 at the 162nd Annual Meeting of the American Psychiatric Association (APA), San Francisco, California, USA, May 16-21, 2009.
Samtani MN, Haskins JT, Gopal S, Sliwa JK, Alphs L, Stuyckens K, Vermeulen a Dosing Information for Paliperidone Palmitate—a Once-Monthly Injectable Atypical Antipsychotic—Based on Population Pharmacokinetic Analysis. Poster NO-310 at the 22nd US Psychiatric and Mental Health Congress (USPMHC), Las Vegas, Nevada, USA, Nov. 2-5, 2009.
Samtani MN, Haskins JT, Gopal S, Sliwa JK, Alphs L, Stuyckens K, Vermeulen a Dosing Information for Paliperidone Palmitate Based on Population Pharmacokinetic Analysis—a Once-Monthly Injectable Atypical Antipsychotic. 22nd US Psychiatric and Mental Health Congress (USPMHC), Las Vegas, Nevada, USA, Nov. 2-5, 2009.
Samtani MN, Sliwa JK, Haskins JT, Alphs L, Stuyckens K, Herben V, Vermeulen a Initiation Dosing of Deltoid Intramuscular Paliperidone Palmitate in Schizophrenia: Pharmacokinetic Rationale Based on Modeling and Simulation. Poster NO-19 at the 12th Annual Meeting of the College of Psychiatric and Neurologic Pharmacists (CPNP), Jacksonville, Florida, Apr. 19-22, 2009.
Samtani MN, Sliwa JK, Haskins JT, Alphs L, Stuyckens K, Herben V, Vermeulen A, Initiation Dosing of Deltoid Intramuscular Paliperidone Palmitate in Schizophrenia: Pharmacokinetic Rationale Based on Modeling and Simulation, 12th Annual Meeting of the College of Psychiatric and Neurologic Pharmacists (CPNP), Jacksonville, Florida, Apr. 19-22, 2009, Journal of Pharmacy Practice 22 (2), p. 216-217 [ERRATUM: 22 (4), p. 432], 2009.
Samtani MN, Vermeulen A, Stuyckens K, Population Pharmacokinetics of Intramuscular Paliperidone Palmitate in Patients with Schizophrenia a Novel Once-Monthly, Long-Acting Formulation of an Atypical Antipsychotic, Clinical Pharmacokinetics 48 (9), p. 585-600, 2009.
Sikirica M, Crivera C, Dirani R, Cost-Effectiveness of Paliperidone Palmitate Versus Oral Atypicals in the US. Poster NO-NR6-5 at the 163rd Annual Meeting of the American Psychiatric Association (APA), New Orleans, Louisiana, USA, May 22-26, 2010.
Singer B Pharmacist Administration of Long-Acting Antipsychotic Injections in a Community Setting. Poster at the 13th Annual Meeting of the College of Psychiatric and Neurologic Pharmacists (CPNP), San Antonio, Texas, USA, Apr. 18-21, 2010.
Sliwa JK, Bossie CA, MA YW, Alphs L, Haskins JT Effects of Paliperidone Palmitate Treatment in Schizophrenia Patients Previously Treated with Oral Risperidone. Poster NO-NR6-17 at the 163rd Annual Meeting of the American Psychiatric Association (APA), New Orleans, Louisiana, USA, May 22-26, 2010.
Sliwa JK, Samtam MN, Haskins JT, Alphs L, Stuyckens K, Herben V, Vermeulen A, Initiation Dosing of Deltoid Intramuscular Paliperidone Palmitate in Schizophrenia: Pharmacokinetic Rationale Based on Modeling and Simulation, 162nd Annual Meeting of the American Psychiatric Association (APA), San Francisco, California, USA, May 16-21, 2009, Proceedings/Abstractbook, p. 19, NO-NR1-046, 2009.
Tandon R, Pharmacologic Treatment of Schizophrenia: Current Status and Future Trends, Current Psychosis and Therapeutics Reports 4, p. 40-49, 2006.
Tomillero A, Moral MA, Gateways to Clinical Trials. Jul.-Aug. 2008, Methods and Findings in Experimental and Clinical Pharmacology 30 (6), p. 459-495, 2008.
Tschoner A, Fleischhacker WW, Ebenbichler CF, Experimental Antipsychotics and Metabolic Adverse Effects—Findings From Clinical Trials, Current Opinion in Investigational Drugs 10 (10), p. 1041-1048, 2009.
Turkoz I, Bossie CA, Dirks B, Canuso CM, Direct and Indirect Effects of Paliperidone Extended-Release Tablets on Negative Symptoms of Schizophrenia, Neuropsychiatric Disease and Treatment 4 (5), p. 949-958, 2008.
Turner N, Bossie CA, Haskins JT, Kern Sliwa J, MA YW, Alphs L Effects of Paliperidone Palmitate in Acutely Ill Subjects With a Marked to Severe Exacerbation of Schizophrenia. Poster NO-NR6-26 at the 163rd Annual Meeting of the American Psychiatric Association (APA), New Orleans, Louisiana, USA, May 22-26, 2010.
Zacher JL, Grady SE, Paliperidone Extended-Release Tablets (INVEGA), Psychopharm Review 42 (7), p. 51-58, 2007.
Alonso, Maria J.; Losa, Candida; Calvo, Pilar; Vila-Jato, Jose L., Approaches to improve the association of amikacin sulfate to poly(alkyl cyanoacrylate) nanoparticles; International Journal of Pharmaceutics (1991), 68(1-3), 69-76.
Bodmeier, Roland; Chen, Huagang, Indomethacin polymeric nanosuspensions prepared by microfluidization, Journal of Controlled Release (1990), 12(3), 223-33.
Coffin, Mark D.; McGinity, James W., Biodegradable Pseudolatexes: The Chemical Stability of Poly(D,L-Lactide) and Poly($\epsilon$-Caprolactone) Nanoparticles in Aqueous Media, Pharmaceutical Research (1992), 9(2), 200-5.
Guise, Veronique; Drouin, Jehan Yves; Benoit, Jacqueline; Mahuteau, Jacqueline; Dumont, Pierre; Couvreur, Patrick, Vidarabine-loaded nanoparticles: a physicochemical study, Pharmaceutical Research (1990), 7(7), 736-41.
Khmelnitskii, Yu. L.; Neverova, I. N.; Gedrovich, A. V.; Polyakov, V. A.; Levashov, A. V.; Martinek, Karel, Catalysis by $\alpha$-chymotrypsin entrapped into surface-modified polymeric nanogranules in organic solvent, European Journal of Biochemistry (1992), 210(3), 751-7.
Khmelnitskii, Yu. L.; Neverova, I. N.; Momcheva, R.; Yaropolov, A. I.; Belova, A. B.; Levashov, A. V.; Martinek, Karel, Surface-modified polymeric nanogranules containing entrapped enxymes: a novel biocatalyst for use in organic media, Biotechnology Techniques (1989), 3(4), 275-80.
Koosha, F.; Muller, R. H.; Davis, S. S.; Davies, M. C., The surface chemical structure of poly($\beta$-hydroxybutyrate) microparticles produced by solvent evaporation process, Journal of Controlled Release (1989), 9(2), 149-57.
Lostritto, R. T.; Goei, L.; Silvestri, S. L., Theoretical considerations of drug release from submicron oil-in-water emulsions, Journal of Parenteral Science and Technology (1987), 41(6), 214-19.
Lostritto, R. T.; Silvestri, S. L., Temperature and cosurfactant effects on lidocaine release from submicron oil-in-water emulsions Journal of Parenteral Science and Technology (1987), 41(6), 220-4.
McLeod, A. D.; Lam, F. C.; Gupta, P. K.; Hung, C. T., Optimized synthesis of polyglutaraldehyde nanoparticles using central composite design, Journal of Pharmaceutical Sciences (1988), 77(8), 704-10.
Rolland, A.; Gibassier, D.; Sado, P.; Le Verge, R., Journal de Pharmacie de Belgique (1986), 41(2), 83-93, Preparation methodology of polyacrylic-based nanoparticle carriers, Laboratory Pharm. Galenique, University Rennes, Rennes, F-35000, Fr. (see English Summary as provided).
Silvestri, Shawn; Wu, Li Li; Bowser, Bill Journal of Pharmaceutical Sciences, Release of polyionizable compounds from submicrometer oil-in-water emulsions, (1992), 81(5), 413-18.
Troester, S. D.; Kreuter, Contact angles of surfactants with a potential to alter the body distribution of colloidal drug carriers on poly(methyl methacrylate) surfaces, J. International Journal of Pharmaceutics (1988), 45(1-2), 91-100.
Alen et al., Ansel's Pharmaceutical Dosage Forms and Drug Delivery Systems, 8th Edition, 2005; pp. 260-263, 652-653, 682.
Alphs et al., "Are the Long-Acting Intramuscular Formulations of Risperidone or Paliperidone Palmitate Associated with Post-Injection Delirium/Sedation Syndrome? An Assessment of Safety Databases", Current Drug Safety, 2011, 6, 43-45.
Alphs et al., "Paliperidone Palmitate Versus Risperidone Long-Acting Therapy in Markedly to Severely Ill Subjects With Schizophrenia", Poster presented at the 23rd Annual US Psychiatric and Mental

(56) References Cited

OTHER PUBLICATIONS

Health Congress; Supported by Ortho-McNeil Janssen Scientific Affairs, LLLC Nov. 18-21, 2010; Orlando, FL, USA.
Alphs et al., "Tolerability of Paliperidone Palmitate Initiation Doses in Subjects with Recently Diagnosed Schizophrenia", Poster handout presented at the Scientific Program of XXVII CINP Congress, Hong Kong. Jun. 6-10, 2010.
Alphs et al., "Tolerability of Paliperidone Palmitate Initiation Doses in Subjects with Recently Diagnosed Schizophrenia", Poster presented at the Scientific Program of XXVII CINP Congress, Hong Kong. Jun. 6-10, 2010.
Altamura et al., Intramuscular preparations of antipsychotics: uses and relevance in clinical practice. Drugs. 2003; 63(5): 493-512.
Canuso et al., Expert Opin. Pharmacother. (2010) 11(15), pp. 2557-2567.
Cleton et al., Clinical Pharmacology & Therapeutics, Mosby-Year Book, St. Louis, MO, US, vol. 81, No. Suppl. 1, p. S63 (2007).
Cockcroft et al., Prediction of creatinine clearance from serum creatinine, Nephron, 16:31-41, 1976.
Ereshefsky L., Pharmacokinetics and drug interactions: update for new antipsychotics. J Clin Psychiatry. 1996;57 Suppl 11:12-25.
Fleischhacker, W. Wolfgang et al., "A randomized trial of paliperidone palmitate and risperidone long-acting injectable in schizophrenia", International Journal of Neuropsychopharmacology, pp. 1-12, CINP 2011.
Gefvert et al. Pharmacokinetics and D2 receptor occupancy of long-acting injectable risperidone (Risperdal Consta) in patients with schizophrenia. Int J Neuropsychopharmacol. 2005; 8(1): 27-36.
Gopal et al., "A 52-week open-label study of the safety and tolerability of paliperidone palmitate in patients with schizophrenia", *J Psychopharmacol*. 2010; First View: 1-13.
Gopal et al., "Dosing Information for Paliperidone Palmitate—A Once-Monthly Injectable Atypical Antipsychotic—Based on Population Pharmacokinetic Analysis", Poster presented at the Scientific Program of XXVII CINP Congress, Hong Kong. Jun. 6-10, 2010.
Gopal et al., "Efficacy and safety of paliperidone palmitate in adult patients with acutely symptomatic schizophrenia: a randomized, double-blind, placebo-controlled, dose-response study", International Clinical Psychopharmacology 2010, vol. 25 No. 5, pp. 247-256.
Gopal et al., Risk of Cardiovascular Morbidity and Sudden Death with Risperidone and Paliperidone Treatment: Analysis of 64 Randomized, Double-Blind Trials, NR 10-24 Presented at the 164th Annual Meeting—American Psychiatric Association, May 14-18, 2011; Honolulu, Hawaii.
Guidance Document: Patented Medicines (Notice of Compliance) Regulations, Health Canada, Nov. 12, 2010.
Kane et al., Guidelines for depot antipsychotic treatment in schizophrenia. European Neuropsychopharmacology Consensus Conference in Siena, Italy. Eur Neuropsychopharmacol. 1998; 8(1): 55-66.
Levron et al., Clinical pharmacokinetics of haloperidol decanoate. Comparison with other prolonged-action neuroleptics. Encephale. 1987; 13(2): 83-7 [see English Summary as provided].
Li et al., "A Comparative Randomized, Open-label, Rater-blinded Study of Paliperidone Palmitate and Risperidone Long-Acting Injectable Therapy in Patients with Schizophrenia", Poster No. P-11-005 presented at the XXVII CINP Congress, Jun. 6-10, 2010; Hong Kong.
Mauri et al., Clinical pharmacokinetics of atypical antipsychotics: a critical review of the relationship between plasma concentrations and clinical response. Clin Pharmacokinet. 2007;46(5):359-88.
Nasrallah et al., "A Controlled, Evidence-Based Trial of Paliperidone Palmitate, A Long-Acting Injectable Antipsychotic, in Schizophrenia", Neuropsychopharmacology (2010) 35, 2072-2082.
Pandina et al., "A double-blind study of paliperidone palmitate and risperidone long-acting injectable in adults with schizophrenia", Progress in Neuro-Psychopharmacology & Biological Psychiatry 2011:35:218-226.
Samtani et al., "Dosing and Switching Strategies for Paliperidone Palmitate", CNS Drugs 2011; 25(10): 829-845.

Samtani et al., "Expansion of Paliperidone Palmitate Day 8 Dose Window from ± 2 Days to ± 4 Days: Model-Based Pharmacokinetic Simulation and Safety Data", Poster presented at the 24th Annual U.S. Psychiatric and Mental Health Congress Meeting, Nov. 7-10, 2011, Las Vegas, Nevada.
Samtani et al., "Expansion of Paliperidone Palmitate Day 8 Dose Window from ± 2 Days to ± 4 Days: Model-Based Pharmacokinetic Simulation and Safety Data", Poster handout presented at the 24th Annual U.S. Psychiatric and Mental Health Congress Meeting, Nov. 7-10, 2011, Las Vegas, Nevada.
Samtani et al., "Switching to Paliperidone Palmitate1,2 from Other Depot Antipsychotics Guidance Based on Pharmacokinetic Simulations", Population Approach Group in Europe, Applications-CNS (Group IV) Abstr 1839, Berlin, Germany. Jun. 8-11, 2010.
Samtani, Mahesh N., "Use of Model Based Simulations to Support the Paliperidone Palmitate Label", AAPS Workshop on Facilitating Oral Product Development and Reducing Regulatory Burden through Novel Approaches to Assess Bioavailability/Bioequivalence, Oct. 22-23, 2011, Washington.
Sheehan et al., "The Management of Antipsychotic Treatment Discontinuation and Interruptions Using Model-Based Simulations", Poster presented at the 51st Annual NCDEU New Research Approaches for Mental Health Interventions Meeting, Jun. 13-16, 2011, Boca Raton, Florida.
Sliwa et al., "Tolerability and Efficacy of Paliperidone Palmitate vs Risperidone Long-acting Injection in Subjects with Recently Diagnosed Schizophrenia", Presented at the 13th International Congress on Schizophrenia Research; Apr. 2-6, 2011; Colorado Springs, Colorado, USA.
Vermeir et al., Absorption, metabolism, and excretion of paliperidone, a new monoaminergic antagonist, in humans. Drug Metab Dispos. Apr. 2008;36(4):769-79.
Alphs et al,, "Onset and persistence of efficacy by symptom domain with long-acting injectable paliperidone palmitate in patients with schizophrenia", Expert Opin. Pharmacother., (2014) 15(7):1029-1042.
William Wilson et al., Mathematical Modeling of Paliperidone Palmitate: A Visual Guide to Expected Blood Levels in Clinical Practice Scenarios, Presented at the 166th Annual Meeting of the American Psychiatric Association, San Francisco, California, May 18-22, 2013.
Gregoriadis et al., Targeting of Drugs 6 Strategies for Stealth Therapeutic Systems: Life Science, 1998, vol. 300, pp. 4-5.
Restriction Requirement dated Mar. 3, 2011 for U.S. Appl. No. 12/305,276.
Non-Final Office Action dated May 4, 2011 for U.S. Appl. No. 12/305,276.
Final Rejection dated Oct. 7, 2011 for U.S. Appl. No. 12/305,276.
Non-Final Office Action dated May 23, 2014 for U.S. Appl. No. 12/305,276.
Gregoriadis et al. (eds.), Targeting of Drugs 6, "Coating of Nanoparticles with Surfactants: Targeting Versus Prolonged Circulation", pp. 253-261 (1998).
J. Zuidema, F. Kadir, H.A.C. Titulaer, C. Oussoren, Release and absorption rates of intramuscularly and subcutaneously injected pharmaceuticals (II), Int. J. Pharm. 105 (1994) 189-207.
K. Hirano, T. Ichihashi, H. Yamada, Studies on the absorption of practically water-insoluble drugs following injection. II. Intramuscular absorption from aqueous suspensions in rats, Chem. Pharm. Bull. (Tokyo). 29 (1981) 817-827.
K. Hirano, H. Yamada, Studies on the absorption of practically water-insoluble drugs following injection. IV. An approach for predicting relative intramuscular absorption rates of a drug in oily solution, aqueous suspension and aqueous surfactant solution in rats, Chem. Pharm. Bull. (Tokyo). 29 (1981) 1410-1415.
J. Zuidema, F.A.J.M. Pieters, G.S.M.J.E. Duchateau, Release and absorption rate aspects of intramuscularly injected pharmaceuticals, Int. J. Pharm. 47 (1988) 1-12.
B.E. Ballard, E. Nelson, Absorption of implanted solid drug, J. Pharm. Sci. 51 (1962) 915-924.

(56) References Cited

OTHER PUBLICATIONS

F.D. Anderson, D.F. Archer, S.M. Harman, R.J. Leonard, W.H. Wilborn, Tissue response to bioerodible, subcutaneous drug implants: a possible determinant of drug absorption kinetics, Pharm. Res. 10 (1993) 369-380.
N. van Rooijen, J. Bakker, A. Sanders, Transient supression of macrophage functions by liposome-encapsulated drugs, Trends Biotechnol. 15 (1997) 178-185.
F. Kadir, J. Zuidema, A. Pijpers, A. Vulto, J.H. Verheijden, The role of drug lipophilicity in release from intra-adipose and intramuscular injection sites, Eur. J. Drug Metab. Pharmacokinet. Spec No. 3 (1991) 146-149.
C.A. Lipinski, F. Lombardo, B.W. Dominy, P.J. Feeney, Experimental and computational approaches to estimate solubility and permeability in drug discovery and development settings, Adv. Drug Deliv. Rev. 23 (1997) 3-25.
Invalidation trial against Korean Patent No. 10-365077; Demandant: Yuhan Corp.; see attached English translation of trial brief as filed.
Invalidation trial against Korean Patent No. 10-365077; Demandant: Dae Woong Parm Co., Ltd.; see attached English translation of trial brief as filed.
Invalidation trial against Korean Patent No. 10-358373; Demandant: Yuhan Corp.; see attached English translation of trial brief as filed.
Invalidation trial against Korean Patent No. 10-358373; Demandant: Dae Woong Pharm Co., Ltd.; see attached English translation of trial brief as filed.
Alonso, M. J.; Losa, C.; Seijo, B.; Torres, D.; Vila Jato, J. L., "New ophthalmic drug release systems, formulation and ocular disposition of amikacin-loaded nanoparticles", Dep. Farmacol., Farm. Technol. Farm., University Santiago de Compostela, Santiago de Compostela, Spain, Congr. Int. Technol. Pharm., 5th (1989), vol. 1, 77-83 Publisher: Associate Pharm. Galenique Ind., Chatenay Malabry, Fr.
Rossenu et al., Evaluation of the Pharmacokinetic Profile of Gluteal Versus Deltoid Intramuscular Injections of Paliperidone Palmitate 100 MG Equivalent in Patients with Schizophrenia, (PI-75) Clinical pharmacology & Therapeutics, vol. 83 Supplement 1, Mar. 2008, S31.
Turkoz et al. BMC Psychiatry 2011, 11:21, pp. 1-10.
Invalidation trial against Korean Patent No. 10-365077; Demandant: Yuhan Corp.; see attached English translation of Response to Trial Brief filed Jul. 10, 2015; Invalidation Trial No. 2015 Dang 2903.
Invalidation trial against Korean Patent No. 10-365077l Demandant: Dae Woong Pharm Co., Ltd.; translation of Response to Trial Brief filed Jul. 10, 2015; Invalidation Trial No. 2015 Dang 2903.
Invalidation trial against Korean Patent No. 10-358373; Demandant: Yuhan Corp.; see attached English translation of Response to Trial Brief filed Jul. 21, 2015; Invalidation Trial No. 2015 Dang 2904.
Invalidation trial against Korean Patent No. 10-358373; Demandant: Dae Woong Pharm Co., Ltd.; see attached English translation of Response to Trial Brief filed Jul. 22, 2015; Invalidation Trial No. 2015 Dang 3000.

\* cited by examiner

AQUEOUS SUSPENSIONS OF SUBMICRON 9-HYDROXYRISPERIDONE FATTY ACID ESTERS

CROSS REFERENCE TO RELATED APPLICATIONS

This application is a continuation of U.S. application Ser. No. 10/383,118, filed Mar. 6, 2003, which is a continuation of U.S. application Ser. No. 09/530,687, filed Nov. 10, 1998, now issued U.S. Pat. No. 6,555,544, which is a National Stage application under 35 U.S.C. §371 of PCT/EP98/07321 filed Nov. 10, 1998, which claims priority from EP 97.203.568.7, filed Nov. 17, 1997, the content of each of these applications is hereby expressly incorporated herein by reference in their entirety.

The present invention is concerned with a pharmaceutical composition suitable as a depot formulation for administration via intramuscular or subcutaneous injection, comprising:
(1) as an active ingredient a therapeutically effective amount of a 9-hydroxyrisperidone fatty acid ester or a salt, or a stereoisomer or a stereoisomeric mixture thereof in submicron form and
(2) a pharmaceutically acceptable carrier; wherein the pharmaceutically acceptable carrier is water and the active ingredient is suspended therein;
and with a process of preparing such a composition.

The invention further involves such a pharmaceutical composition for use as a medicament in the treatment of psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety.

Risperidone is generic to 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one. The preparation and pharmacological activity thereof are described in EP-0,196,132 (corresponding to U.S. Pat. No. 4,804,663). Various conventional pharmaceutical dosage forms, including tablets, capsules, drops, suppositories, oral solutions and injectable solutions are exemplified therein. In practice, risperidone is normally administered as the base in a tablet or in a buffered, oral or intramuscular solution. Particular solutions for oral or intramuscular administration are described in WO-96/01652.

Risperidone is a highly potent drug having a relatively narrow therapeutic index. It may produce undesirable side effects on overdosage, most notably extra pyramidal syndrome (EPS) and to a lesser extent hypotension (due to peripheral alpha-adrenergic activity). For the purpose of producing an antipsychotic effect in a patient the total daily dose of risperidone ranges from about 2 to about 8 mg; for the alleviation of behavioral disturbances associated with neurodegenerative disorders the total daily dose is usually less and typically ranges from about 0.5 to about 2 mg. Inter-individual differences and co-medication may necessitate dose titrating in patients.

It is known that risperidone is metabolized to 9-hydroxyrisperidone which has a pharmacological profile and potency comparable with that of the parent drug risperidone, but which has a longer elimination half-life. Risperidone is distributed to and eliminated from the brain tissues more rapidly than its metabolite 9-hydroxyrisperidone. 9-hydroxyrisperidone, its enantiomeric forms and the $C_{2-20}$ alkanoic acid esters thereof are described in EP-0,368,388 (corresponding to U.S. Pat. No. 5,158,952 and U.S. Pat. No. 5,254,556). Said esters are considered to be potentially valuable prodrugs of the active metabolite of risperidone for use in depot formulations.

For a number of reasons, it is desirable to administer risperidone in a sustained or delayed release (depot) formulation which is effective over an extended period of time, preferably about 3 weeks or more, in particular about 1 month.

WO-94/25460 (corresponding to EP-0,697,019) relates to a first such depot formulation and concerns the risperidone pamoate salt, a poorly water-soluble salt form of risperidone, which may be suspended in a pharmaceutically acceptable carrier, such as water or an oil, and may be administered subcutaneously or intramuscularly. This salt, however, has pharmacokinetic properties which are suboptimal. The release of the active ingredient from the formulations appears to be too rapid, which results in relatively high initial plasma levels and an inadequate mean duration of action, both characteristics which should be improved upon in a truly effective depot formulation.

WO-95/13814 concerns sustained release formulations for parenteral administration wherein risperidone is microencapsulated in a biocompatible, biodegradable wall-forming material (e.g. a polymer such as dl-(polylactide-co-glycolide)). The microencapsulated formulations have suitable pharmacokinetic properties, but require sophisticated processes of preparation in a purpose-built plant.

PCT/EP97/02504 discloses aqueous suspensions of 9-hydroxyrisperidone fatty acid esters in water wherein the prodrug of the active ingredient is in micronized form. Unexpectedly, these formulations prove to be far too longlasting in humans to be therapeutically useful.

Consequently, there is still a need for an effective and readily available depot formulation of risperidone or a risperidone-like compound.

Nanoparticles are well known in the prior art, having been described, for example, in EP-A-0,499,299. These particles consist essentially of a crystalline drug substance having a surface modifier absorbed on the surface of the particles such that the effective average particle size is less than about 400 nm. It is also known that said particles are particularly useful to formulate poorly water soluble active ingredients.

The present invention results from the investigations into the development of an efficient, well-tolerated, sustained or delayed release (depot) formulation of a 9-hydroxyrisperidone alkanoic acid ester which is therapeutically effective for at least three weeks or more, in particular about 1 month. By the expression "effective for at least three weeks or more", one means that the plasma level of the active ingredient, 9-hydroxyrisperidone (free alcohol liberated by hydrolysis from the alkanoic acid ester), should be above approximately 10 ng/ml. On the other hand, said plasma level should remain at all times below a threshold value of approximately 100 ng/ml in order for one to call the formulation "efficient". The threshold value is the mean plasma level during a considerable period of time, e.g. for more than 15 minutes, above which patients may experience undesirable side effects, or conversely, the value of the plasma level under which the systemic tolerance of the formulation in question is still acceptable. The threshold value does not hold for transient, high plasm levels during a short period of time, e.g. for less than 15 minutes, which are due, for example to unexpected burst-release of the active ingredient.

Both of the foregoing features—plasma levels above a minimal therapeutical concentration but below a side-effect producing threshold value—are considered to be basic requirements that a contemporary depot formulation should fulfil in order to be acceptable for the intended patients.

Limiting the number of drug administrations and the occurrence of undesirable side effects after each administration will undoubtedly improve the patients' compliance with the therapy. However, beyond these basic requirements, a number of further desiderata can be identified which would further improve patients' compliance; the two most notable being good local tolerance and ease of administration.

Good local tolerance means minimal irritation and inflammation at the site of injection; ease of administration refers to the size of needle and length of time required to administer a dose of a particular drug formulation. In addition, depot formulations should be stable and have a shelf-life of at least two years under normal conditions.

The investigations into the development of an efficient, well-tolerated, sustained or delayed release (depot) formulation of a 9-hydroxyrisperidone alkanoic acid ester which fulfils the above mentioned requirements, led to the finding that a pharmaceutical composition suitable as a depot formulation for administration by intramuscular or subcutaneous injection should comprise:

a dispersion of particles consisting essentially of a therapeutically effective amount of a crystalline 9-hydroxyrisperidone fatty acid ester having the formula

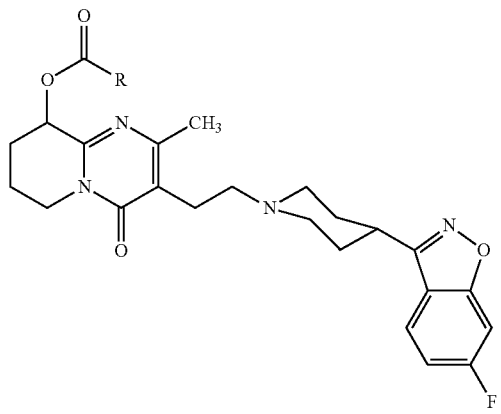

or a salt, or a stereoisomer or a stereoisomeric mixture thereof, wherein R represents a straight $C_{9-19}$alkyl radical; having a surfactant absorbed to the surface thereof in an amount effective in maintaining a specific surface area >4 $m^2/g$ (corresponding to an effective average particle size of less than 2,000 nm), in a pharmaceutically acceptable carrier comprising water.

Surprisingly, it appears that aqueous suspensions of micronized 9-hydroxyrisperidone $C_{10-20}$ alkanoic acid esters (wherein R represents a straight $C_{9-19}$ alkyl radical) have an exceptionally longlasting effect in humans, but not in test animals, in particular dogs. This is quite unexpected since the pharmacokinetics of drugs in humans and in dogs are often comparable. The pharmacokinetic properties in humans of the aqueous suspensions of 9-hydroxyrisperidone alkanoic acid esters depend on the particle size to a much larger extent than previously held possible.

$C_{10-20}$alkanoic acids are selected from the group consisting of decanoic (capric), undecanoic, dodecanoic (lauric), tridecanoic, tetradecanoic (myristic), pentadecanoic, hexadecanoic (palmitic), heptadecanoic, octadecanoic (stearic), nonadecanoic and eicosanoic acid. The ester having a $C_{15}$ (pentadecyl) chain and the active ingredient corresponding thereto being the 9-hydroxyrisperidone palmitate ester was found to be the superior ester from a pharmacokinetic, as well as from a tolerance point of view.

The nanoparticles of the present invention have a surfactant or surface modifier adsorbed on the surface thereof in an amount sufficient to maintain a specific surface area >4 $m^2/g$ (i.e. corresponding to an average particle size of less than 2,000 nm), preferably the specific surface area >6 $m^2/g$, and in particular is in the range from 10 to 16 $m^2/g$. Useful surface modifiers are believed to include those which physically adhere to the surface of the active agent but do not chemically bond thereto.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alcyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminate silicate, triethanolamine, polyvinyl alcohol (PVA), poloxamers, tyloxapol and polyvinylpyrrolidone (PVP). Most of these excipients are described in detail in the *Handbook of Pharmaceutical Excipients*, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone; tyloxapol; poloxamers, such as Pluronic™ F68, F108 and F127 which are block copolymers of ethylene oxide and propylene oxide available from BASF; poloxamines, such as Tetronic™ 908 (T908) which is a tetrafunctional block copolymer derived from sequential addition of ethylene oxide and propylene oxide to ethylenediamine available from BASF; dextran; lecithin; Aerosol OT™ (AOT) which is a dioctyl ester of sodium sulfosuccinic acid available from Cytec Industries; Duponol™ P which is a sodium lauryl sulfate available from DuPont; Triton™ X-200 which is an alkyl aryl polyether sulfonate available from Rohm and Haas; Tweens™ 20, 40, 60 and 80 which are polyoxyethylene sorbitan fatty acid esters available from ICI Speciality Chemicals; Span™ 20, 40, 60 and 80 which are sorbitan esters of fatty acids; Arlacel™ 20, 40, 60 and 80 which are sorbitan esters of fatty acids available from Hercules, Inc.; Carbowax™ 3550 and 934 which are polyethylene glycols available from Union Carbide; Crodesta™ F110 which is a mixture of sucrose stearate and sucrose distearate available from Croda Inc.; Crodesta™ SL-40 which is available from Croda, Inc.; hexyldecyl trimethyl ammonium chloride (CTAC); bovine serum albumin and SA90HCO which is $C_{18}H_{17}CH_2$ $(CON(CH_3)CH_2(CHOH)_4CH_2OH)_2$. The surface modifiers which have been found to be particularly useful include tyloxapol and a poloxamer, preferably, Pluronic™ F 108 and Pluronic™ F 68.

Pluronic™ F108 corresponds to poloxamer 338 and is the polyoxyethylene, polyoxypropylene block copolymer that conforms generally to the formula $HO[CH_2CH_2O]_x[CH(CH_3)CH_2O]_y[CH_2CH_2O]_zH$ in which the average values of x, y and z are respectively 128, 54 and 128. Other commercial names of poloxamer 338 are Hodag Nonionic™ 1108-F available from Hodag, and Synperonic™ PE/F108 available from ICI Americas.

The optimal relative amount of the antipsychotic agent and the surface modifier depends on various parameters. The optimal amount of the surface modifier can depend, for example, upon the particular antipsychotic agent and surface modifier selected, the critical micelle concentration of the surface modifier if it forms micelles, the surface area of the antipsychotic agent, etc. The specific surface modifier preferably is present in an amount of 0.1 to 1 mg per square meter surface area of the antipsychotic agent. In case 9-hydroxyrisperidone palmitate is used as antipsychotic agent and Pluronic™ F108 as a surface modifier, a relative amount (w/w) of both ingredients of approximately 6:1 is preferred.

As used herein, an effective average particle size of less than 2,000 nm means that at least 90% of the particles have a diameter of less than 2,000 nm when measured by art-known conventional techniques, such as sedimentation field flow fractionation, photon correlation spectroscopy or disk centrifugation. With reference to the effective average particle size, it is preferred that at least 95% and, more preferably, at least 99% of the particles have a particle size of less than the effective average particle size, e.g. 2,000 nm. Most preferably, essentially all of the particles have a size of less than 2,000 nm.

The particles of this invention can be prepared by a method comprising the steps of dispersing an antipsychotic agent in a liquid dispersion medium and applying mechanical means in the presence of grinding media to reduce the particle size of the antipsychotic agent to an effective average particle size of less than 2,000 nm. The particles can be reduced in size in the presence of a surface modifier. Alternatively, the particles can be contacted with a surface modifier after attrition.

A general procedure for preparing the particles of this invention includes
(a) obtaining an antipsychotic agent in micronized form;
(b) adding the micronized antipsychotic agent to a liquid medium to form a premix; and
(c) subjecting the premix to mechanical means in the presence of a grinding medium to reduce the effective average particle size.

The selected antipsychotic agent in micronized form is obtained commercially or prepared using techniques known in the art. It is preferred that the particle size of the micronized antipsychotic agent be less than about 100 µm as determined by sieve analysis. If the particle size of the micronized antipsychotic agent is greater than about 100 µm, then it is preferred that the particles of the antipsychotic agent be reduced in size to less than 100 µm.

The micronized antipsychotic agent can then be added to a liquid medium in which it is essentially insoluble to form a premix. The concentration of the antipsychotic agent in the liquid medium (weight by weight percentage) can vary widely and depends on the selected antipsychotic agent, the selected surface modifer and other factors. Suitable concentrations of antipsychotic agent in compositions vary between 0.1 to 60%, preferably is from 0.5 to 30%, and more preferably, is approximately 7% (w/v).

A more preferred procedure involves the addition of a surface modifier to the premix prior to its subjection to mechanical means to reduce the effective average particle size. The concentration of the surface modifier (weight by weight percentage) can vary from 0.1% to 90%, preferably from 0.5% to 80%, and more preferably is approximately 7% (w/v).

The premix can be used directly by subjecting it to mechanical means to reduce the effective average particle size in the dispersion to less than 2,000 nm. It is preferred that the premix be used directly when a ball mill is used for attrition. Alternatively, the antipsychotic agent and, optionally, the surface modifier, can be dispersed in the liquid medium using suitable agitation such as, for example, a roller mill or a Cowles type mixer, until a homogeneous dispersion is achieved.

The mechanical means applied to reduce the effective average particle size of the antipsychotic conveniently can take the form of a dispersion mill. Suitable dispersion mills include a ball mill, an attritor mill, a vibratory mill, a planetary mill, media mills such as a sand mill and a bead mill. A media mill is preferred due to the relatively shorter milling time required to provide the desired reduction in particle size. For media milling, the apparant viscosity of the premix preferably is anywhere between 0.1 and 1 Pa·s. For ball milling, the apparant viscosity of the premix preferably is anywhere between 1 and 100 mPa·s.

The grinding media for the particle size reduction step can be selected from rigid media preferably spherical or particulate in form having an average size less than 3 mm and, more preferably, less than 1 mm. Such media desirably can provide the particles of the invention with shorter processing times and impart less wear to the milling equipment. The selection of the material for the grinding media is believed not to be critical. However, 95% ZrO stabilized with magnesia, zirconium silicate, and glass grinding media provide particles having levels of contamination which are believed to be acceptable for the preparation of pharmaceutical compositions. Further, other media, such as polymeric beads, stainless steel, titania, alumina and 95% ZrO stabilized with yttrium, are useful. Preferred grinding media have a density greater than 2.5 g/cm$^3$ and include 95% ZrO stabilized with magnesia and polymeric beads.

The attrition time can vary widely and depends primarily upon the particular mechanical means and processing conditions selected. For rolling mills, processing times of up to two days or longer may be required.

The particles must be reduced in size at a temperature which does not significantly degrade the antipsychotic agent. Processing temperatures of less than 30 to 40° C. are ordinarily preferred. If desired, the processing equipment may be cooled with conventional cooling equipment. The method is conveniently carried out under conditions of ambient temperature and at processing pressures which are safe and effective for the milling process.

The surface modifier, if it was not present in the premix, must be added to the dispersion after attrition in an amount as described for the premix above. Thereafter, the dispersion can be mixed by, for example, shaking vigorously. Optionally, the dispersion can be subjected to a sonication step using, for example, a ultrasonic power supply.

Aqueous compositions according to the present invention conveniently further comprise a suspending agent and a buffer, and optionally one or more of a preservative and an isotonizing agent. Particular ingredients may function as two or more of these agents simultaneously, e.g. behave like a preservative and a buffer, or behave like a buffer and an isotonizing agent.

Suitable suspending agents for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxypropylene ethers. Preferably sodium carboxymethyl cellulose is used in a concentration of 0.5 to 2%, most preferably 1% (w/v). Suitable wetting agents for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of 0.5 to 3%, more preferably 0.5 to 2%, most preferably 1.1% (w/v).

Suitable buffering agents are salt of weak acids and should be used in amount sufficient to render the dispersion neutral to very slightly basic (up to pH 8.5), preferably in the pH range of 7 to 7.5. Particularly preferred is the use of a mixture of disodium hydrogen phosphate (anhydrous) (typically about 0.9% (w/v)) and sodium dihydrogen phosphate monohydrate (typically about 0.6% (w/v)). This buffer also renders the dispersion isotonic and, in addition, less prone to flocculation of the ester suspended therein.

Preservatives are antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-γ-piccolinium chloride, phenylmercuric acetate and thimerosal. In particular, it is benzyl alcohol which can be used in a concentration up to 2% (w/v), preferably up to 1.5% (w/v).

Isotonizing agents are, for example, sodium chloride, dextrose, mannitol, sorbitol, lactose, sodium sulfate. The suspensions conveniently comprise from 0 to 10% (w/v) isotonizing agent. Mannitol may be used in a concentration from 0 to 7% More preferably, however, from about 1 to about 3% (w/v), especially from about 1.5 to about 2% (w/v) of one or more electrolytes are used to render the suspension isotonic, apparently because ions help to prevent flocculation of the suspended ester. In particular electrolytes of the buffer serve as isotonizing agent.

A particularly desirable feature for an injectable depot formulation relates to the ease with which it can be administered. In particular such an injection should be feasible using a needle as fine as possible in a span of time which is as short as possible. This can be accomplished with the aqueous suspensions of the present invention by keeping the viscosity below about 75 mPa·s, preferably below 60 mPa·s. Aqueous suspensions of such viscosity or lower can both easily be taken up in a syringe (e.g. from a vial), and injected through a fine needle (e.g a 21 G1½, 22 G 2 or 22 G 1¼ needle).

Ideally, aqueous suspensions according to the present invention will comprise as much prodrug as can be tolerated so as to keep the injected volume to a minimum, and as little of the other ingredients as possible. In particular, such a composition will comprise by weight based on the total volume of the composition:
(a) from 3 to 20% (w/v) of the prodrug;
(b) from 0.5 to 2% (w/v) of a wetting agent;
(c) one or more buffering agents sufficient to render the composition neutral to very slightly basic (pH 8.5);
(d) from 0.5 to 2% (w/v) of a suspending agent;
(e) up to 2% (w/v) preservatives; and
(f) water q.s. ad 100%.

In view of the usefulness of 9-hydroxyrisperidone in the treatment of a number of disorders, the present invention also concerns a pharmaceutical composition as described hereinbefore for use as a medicament in the treatment of psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety.

In addition, the present invention concerns the use of a composition as described hereinbefore for the preparation of a medicament for treating psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety.

The present invention further concerns a method of treating warm-blooded animals, in particular humans suffering from psychosis, schizophrenia, schizoaffective disorders, non-schizophrenic psychoses, behavioural disturbances associated with neurodegenerative disorders, e.g. in dementia, behavioural disturbances in mental retardation and autism, Tourette's syndrome, bipolar mania, depression, anxiety, said method comprising the administration of a therapeutically effective amount of an aqueous suspension as described hereinbefore. Typically, said formulation will be administered approximately every three weeks or even at longer intervals where possible. The dosage should range from about 2 to 4 mg/kg body weight.

The following examples are intended to illustrate the present invention.

EXPERIMENTAL PART

A. Preparation of 9-hydroxyrisperidone palmitate ester.

N,N-Dicyclohexylcarbodiimide (1.39 g; 6.8 mmol) was added to a solution of hexadecanoic acid (1.54 g; 6 mmol) in dichloromethane (140 ml) and stirred at room temperature for 10 minutes. 9-hydroxyrisperidone (2.13 g; 5 mmol) was added to the reaction mixture, followed by 4-pyrrolidinopyridine (93 mg; 0.63 mmol). The mixture was stirred for three days at room temperature. Water (200 ml) was added to the reaction mixture and this was extracted three times with chloroform (100 ml). The combined organic layers were dried (MgSO$_4$), filtered, and evaporated. The mixture was triturated in diisopropylether (100 ml), filtered and recrystalized in isopropanol (60 ml). The crystals were filtered off and dried, yielding 9-hydroxyrisperidone palmitate ester (2.67 g; 80.4%).

B. Composition Examples

The formulations hereunder were prepared according to the following general recipe: The surfactant, suspending agent and buffer were dissolved by stirring in water at room temperature and the solution was sterilized by heating during 30 minutes at 121° C. The active ingredient (micronized) was sterilized by gamma irradiation at 25 kGY and suspended in the previously prepared solution under sterile conditions. Appropriate glass vials were filled to about 30% of their total volume with the suspension and with the grinding medium, and then rolled at about 50 rpm for several hours. The submicron formulations were then sieved to remove the grinding medium and stored under sterile conditions. Formulation A (micronized) was rolled for 0 hours, B for 4 hours, C for 7 hours and D for 38 hours.

Formulation (w/v)

| 9-hydroxyrisperidone palmitate | 7.02% (4.5% 9-hydroxyrisperidone) |
| polysorbate 20 | 1.1% |
| sodium carboxymethyl cellulose 30 mPa·s | 1% |
| benzyl alcohol parenteral | 1.5% |
| disodium hydrogen phosphate anhydrous | 0.9% |
| sodium dihydrogen phosphate monohydrate | 0.6% |
| water q.s. ad | 100% |

Viscosity and pH values for each of the thus obtained submicron dispersion A-D were as follows:

| Formulation | pH | viscosity |
| --- | --- | --- |
| A | 8.19 | ±7 mPa·s |
| B | 7.9 | ±8 mPa·s |
| C | 8.02 | ±9 mPa·s |
| D | 7.98 | ±10 mPa·s |

Particle size distribution was measured using a Mastersizer X and specific surface area using a Mastersizer S. The following values were obtained for formulations A-D:

| | Particle size (μm) | | | |
| --- | --- | --- | --- | --- |
| Formulation | 10% | 50% | 90% | specific surface area (m²/g) |
| A | 2.51 | 6.03 | 7.64 | 1.3 |
| B | 0.62 | 1.38 | 6.83 | 6.5 |
| C | 0.52 | 0.74 | 1.15 | 13.5 |
| D | 0.43 | 0.52 | 0.65 | >15 |

Formulations C and D were put on a three month stability test and the following values were obtained for the stored formulations C and D:

| | Particle size (μm) | | | |
| --- | --- | --- | --- | --- |
| Formulation | 10% | 50% | 90% | specific surface area (m²/g) |
| C | 0.27 | 0.40 | 0.62 | 13.5 |
| D | 0.52 | 0.75 | 1.18 | not determined |

C. Pharmacological Examples

C.1. Pharmacological Testing of F1 and Analogous Oil Formulations

Each of the four formulations A-D were administered to four beagle dogs intramuscularly in the m. biceps femuris of the left hind paw at 2.5 mg/kg bodyweight using a 21 G 1½ BD Microlance needle; syringability posed no problem. Blood samples were withdrawn during 2 months in order to determine 9-hydroxy risperidone plasma levels. The following pharmacokinetic parameters were calculated from the experimental data (mean±S.D.):

| formulation | $C_{max}$ (ng/ml) | $T_{max}$ (days) | $AUC_{0-t}$ (ng·h/ml) |
| --- | --- | --- | --- |
| A | 41.1 (±22.1) | 12 (±5) | 19487 (±7697) |
| B | 86.4 (±30.5) | 7 (±3) | 25769 (±9782) |
| C | 139 (±33) | 1.8 (±1.5) | 28603 (±4305) |
| D | 132 (±60) | 6.3 (±1.5) | 34852 (±14055) |

The invention claimed is:

1. An injectable pharmaceutical depot composition suitable as a depot formulation for administration by intramuscular or subcutaneous injection, comprising a dispersion of particles consisting essentially of a therapeutically effective amount of a crystalline 9-hydroxyrisperidone fatty acid ester having the formula

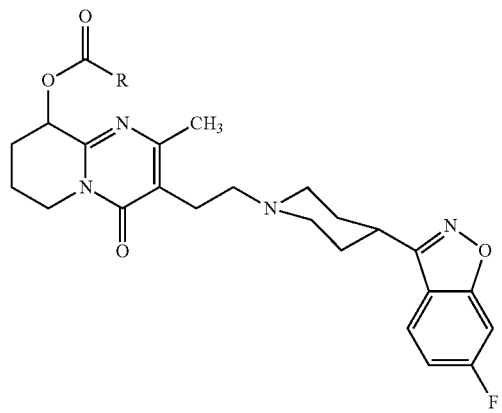

or a salt, or a stereoisomer or a stereoisomeric mixture thereof, wherein R represents a straight $C_{9-19}$ alkyl radical; having a surfactant adsorbed to the surface of the particles in an amount effective to in maintaining a specific surface area of the particles in the range of from 10 to 16 m²/g as measured on a Mastersizer S in a pharmaceutically acceptable carrier comprising water wherein said injectable pharmaceutical depot composition is therapeutically effective for about one month.

2. The injectable pharmaceutical depot composition according to claim 1 wherein R represents a straight $C_{15}$ (pentadecyl) chain and the active ingredient is 9-hydroxyrisperidone palmitate ester.

3. The injectable pharmaceutical depot composition according to claim 2 wherein the composition further comprises a suspending agent.

4. The injectable pharmaceutical depot composition according to claim 3 wherein the suspending agent is polyethylene glycol.

5. The injectable pharmaceutical depot composition according to claim 3 wherein the surfactant is polysorbate 20.

6. The injectable pharmaceutical depot composition according to claim 2 having a viscosity of less than 75 mPa·s.

7. The injectable pharmaceutical depot composition according to claim 6 comprising:
(a) from 3 to 20% (w/v) of a dispersion of particles consisting essentially of a therapeutically effective amount of a crystalline 9-hydroxyrisperidone palmitate ester;
(b) the surfactant adsorbed to the surface thereof of the particles is polysorbate 20;
(c) one or more buffering agents sufficient to render the composition neutral to very slightly basic (up to pH 8.5);

(d) a suspending agent;
(e) up to 2% (w/v) preservatives; and
(f) water q.s. ad 100%.

8. A method for treating a human suffering from psychosis, schizophrenia, schizoaffective disorders, non-schizophrenic psychoses, behavioural disturbances associated with neurodegenerative disorders, bipolar mania, depression, or anxiety comprising administering intramuscularly or subcutaneously the injectable pharmaceutical depot composition of claim 1 to said human.

9. The method of claim 8 wherein 9-hydroxyrisperidone fatty acid ester contained in the composition is 9-hydroxyrisperidone palmitate ester.

10. The method of claim 9 wherein the human is suffering from schizophrenia.

11. The method of claim 9 wherein the human is suffering from schizoaffective disorders.

12. The injectable pharmaceutical depot composition according to claim 7 wherein the suspending agent is polyethylene glycol.

13. The injectable pharmaceutical depot composition of claim 1 wherein 90 percent of the particles are less than 2000nm as measured by a Mastersizer X.

14. An injectable pharmaceutical depot composition suitable as a depot formulation for administration by intramuscular or subcutaneous injection, comprising a dispersion of particles consisting essentially of a therapeutically effective amount of a crystalline 9-hydroxyrisperidone fatty acid ester having the formula

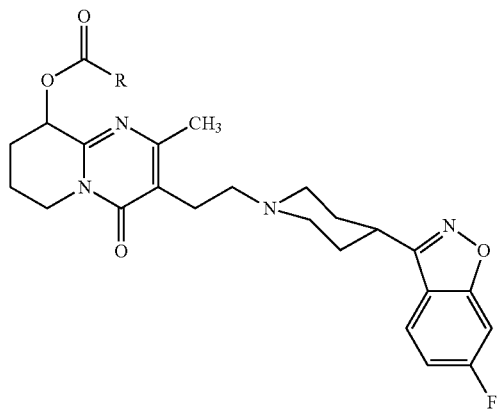

or a salt, or a stereoisomer or a stereoisomeric mixture thereof, wherein R represents a straight $C_{9-19}$ alkyl radical; having a surfactant adsorbed to the surface of the particles in an amount effective in maintaining a specific surface area of the particles in the range of from 10 to 16 m$^2$/g as measured on a Mastersizer S and wherein 90 percent of the particles have a particle size less than 1.15 μm as measured by a Mastersizer X in a pharmaceutically acceptable carrier comprising water wherein said injectable pharmaceutical depot composition is therapeutically effective for about one month.

15. The injectable pharmaceutical depot composition according to claim 14 wherein R represents a straight $C_{15}$ (pentadecyl) chain and the active ingredient is 9-hydroxyrisperidone palmitate ester.

16. The injectable pharmaceutical depot composition according to claim 15 wherein the composition further comprises a suspending agent.

17. The injectable pharmaceutical depot composition according to claim 16 wherein the suspending agent is polyethylene glycol.

18. The injectable pharmaceutical depot composition according to claim 15 wherein the surfactant is polysorbate 20.

19. The injectable pharmaceutical depot composition according to claim 15 having a viscosity of less than 75 mPa·s.

20. The injectable pharmaceutical depot composition according to claim 19 comprising:
(a) from 3 to 20% (w/v) of the 9-hydroxyrisperidone fatty acid ester wherein the 9-hydroxyrisperidone fatty acid ester is 9-hydroxyrisperidone palmitate ester;
(b) wherein the surfactant is polysorbate 20;
(c) one or more buffering agents sufficient to render the composition neutral to very slightly basic (up to pH 8.5);
(d) a suspending agent;
(e) up to 2% (w/v) preservatives; and
(f) water q.s. ad 100%.

21. The injectable pharmaceutical depot composition according to claim 20 wherein the suspending agent is polyethylene glycol.

22. A method for treating a human suffering from psychosis, schizophrenia, schizoaffective disorders, non-schizophrenic psychoses, behavioural disturbances associated with neurodegenerative disorders, bipolar mania, depression, or anxiety comprising administering intramuscularly or subcutaneously the injectable pharmaceutical depot composition of claim 14 to said human.

23. The method of claim 22 wherein 9-hydroxyrisperidone fatty acid ester contained in the composition is 9-hydroxyrisperidone palmitate ester.

24. The method of claim 23 wherein the human is suffering from schizophrenia.

25. The method of claim 23 wherein the human is suffering from schizoaffective disorders.

26. An injectable pharmaceutical depot composition suitable as a depot formulation for administration by intramuscular or subcutaneous injection, comprising a dispersion of particles consisting essentially of a therapeutically effective amount of a crystalline 9-hydroxyrisperidone fatty acid ester having the formula

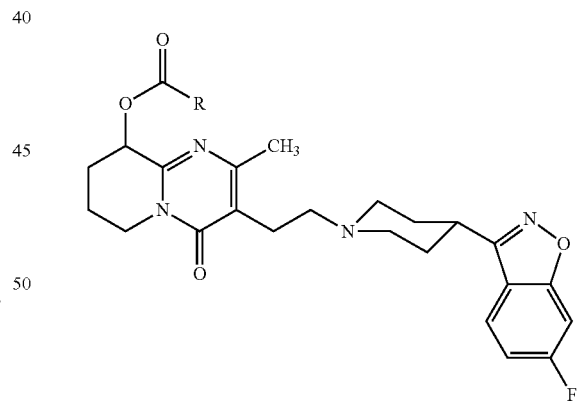

a salt, or a stereoisomer or a stereoisomeric mixture thereof, wherein R represents a straight $C_{9-19}$ alkyl radical; having a surfactant adsorbed to the surface of the particles in an amount effective in maintaining a specific surface area of the particles in the range of from 10 to 16 m$^2$/g as measured on a Mastersizer S and wherein 10 percent of the particles have a particle size less than 0.43 μm as measured by a Mastersizer X in a pharmaceutically acceptable carrier comprising water wherein said injectable pharmaceutical depot composition is therapeutically effective for about one month.

* * * * *